(12) United States Patent
Pamukcu et al.

(10) Patent No.: US 6,562,830 B1
(45) Date of Patent: *May 13, 2003

(54) METHOD OF TREATING A PATIENT HAVING PRECANCEROUS LESIONS WITH PHENYL QUINAZOLINONE DERIVATIVES

(75) Inventors: Rifat Pamukcu, Spring House, PA (US); Gary A. Piazza, Highlands Ranch, CO (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,806

(22) Filed: Nov. 9, 1999

(51) Int. Cl.$^7$ .................. A61K 31/505; A61K 31/495; A61K 31/50; A61K 31/535
(52) U.S. Cl. ................ 514/259; 514/252.14; 514/234.8
(58) Field of Search ........................... 514/259, 252.17, 514/234.8, 254; 374/234.8

(56) References Cited

U.S. PATENT DOCUMENTS 4,950,680 A    8/1990  Taylor et al.
6,187,779 B1 * 2/2001  Pamukcu et al. ........... 514/259

FOREIGN PATENT DOCUMENTS

WO    WO 95/19978    7/1995

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1798, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cells Lines, Science, vol. 275, pp. 1790–1792, Mar. 21, 1997.

* cited by examiner

*Primary Examiner*—Jerome D. Goldberg
(74) *Attorney, Agent, or Firm*—Robert W. Stevenson

(57) ABSTRACT

Derivatives of 2-phenyl quinazolinones are useful for the treatment of patients having precancerous lesions. These compounds are also useful to inhibit growth of neoplastic cells.

3 Claims, No Drawings

METHOD OF TREATING A PATIENT HAVING PRECANCEROUS LESIONS WITH PHENYL QUINAZOLINONE DERIVATIVES

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the 2-phenyl quinazolinone derivative represented by the following formula (I), or the pharmacologically acceptable salt thereof;

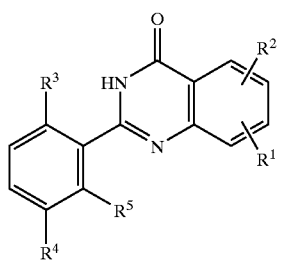

(I)

wherein $R^1$ and $R^2$ are independently hydrogen, lower alkyl, lower alkoxy, lower alkyl thio, nitro, —$CONR^6R^7$, or —$NR^6R^7$; and $R^6$ and $R^7$ are independently hydrogen or lower alkyl optionally substituted by hydroxy provided that the carbon atom adjacent to the nitrogen atom is not substituted by hydroxy;

$R^3$ is hydrogen, lower alkyl or lower alkoxy;

$R^4$ is hydrogen, $C_2$–$C_4$ alkanoyl optionally substituted with $NR^8R^9$, (hydroxy) $C_2$–$C_4$ alkyl optionally substituted with $NR^8R^9$, $CH=CHCO_2R^{10}$, $CH=CHCONR^8R^9$, $CH_2CH_2CO_2R^{10}$, $CH_2CH_2CONR^8R^9$, $SO_2NR^8R^9$, $SO_2NH(CH_2)_nNR^8R^9$ or imidazolyl; and $R^8$ and $R^9$ are independently hydrogen or lower alkyl or together with the nitrogen to which they are attached from a pyrrolidino, piperidino, morpholino or 4-($NR^6$)-1-piperazinyl group wherein any of said groups is optionally substituted with $CONR^6R^7$; and $R^{10}$ is hydrogen, lower alkyl or lower alkoxy; and n is 2, 3 or 4; and $R^5$ is lower alkoxy, lower alkenoxy, cyclo (lower) alkyl (lower) alkoxy, phenyl (lower) alkoxy, or phenyl (lower) alkoxy with the alkoxy substituted by 1 to 6 fluoro groups.

Suitably $R^1$ is hydrogen or $C_{1-6}$alkyl for example methyl or ethyl.

Suitably $R^1$ is $C_{1-6}$alkylthio or $C_{1-6}$ alkoxy for example methylthio, ethylthio, methoxy or ethoxy.

Suitably $R^1$ is nitro or —$NR^3R^4$ for example methylamino, dimethylamino or 2-hydroxyethylamino.

Suitably $R^5$ is $C_2$–$C_5$ alkoxy or $C_3$–$C_5$ alkenoxy.

Suitably $R^5$ is cyclopropylmethoxy or benzoxy.

Preferably $R^5$ is n-propoxy.

Particular compounds of this invention are: 2-(2-propoxyphenyl)quinazolinone-4(3H)-one, 7-methylthio-2-(2-propoxyphenyl)quinazolin-4(3H)-one, 7-nitro-2-(2-propoxyphenyl)-4(3H)-quinazolinone, 7-amino-2-(2-propoxy-phenyl)-4(3H)-quinazolinone, or 7-methylamino-2-(2-propoxyphenyl)-4(3H)-quinazolin one or pharmaceutically acceptable salts thereof.

A preferred group of compounds of formula (I) is that wherein $R^1$ is H, methyl, methoxy or $CONR^6R^7$; $R^2$ is H or methyl; $R^3$ is ethyl or n-propyl; $R^4$ is H, acetyl optionally substituted with $NR^8R^9$, hydroxyethyl substituted with $NR^8R^9$, $CH=CHCO_2R^{10}$, $CH=CHCONR^8R^9$, $CH_2CH_2CO_2R^{10}$, $SO_2NR^8R^9$, $SO_2NH(CH_2)_3NR^8R^9$ or 1-imidazolyl; $R^6$ and $R^7$ are each independently H or ethyl; $R^8$ and $R^9$ together with the nitrogen atom to which they are attached form a piperidino, 4-carbamoylpiperidino, morpholino or 4-($NR^{11}$)-1-piperazinyl group; $R^{10}$ is H or t-butyl; and $R^{11}$ is H, methyl or 2-hydroxyethyl; with the proviso that $R^4$ is not H when $R^1$ is H, methyl or methoxy; and $R^5$ is hydrogen.

A particularly preferred group of compounds of formula (I) is that wherein $R^1$ is methyl, $CONH_2$ or $CONHCH_2CH_3$; $R^2$ is H; $R^3$ is ethyl or n-propyl; $R^4$ is H, acetyl, 1-hydroxy-2-($NR^8R^9$) ethyl, $CH=CHCO_2C(CH_3)_3$, $CH=CHCONR^8R^9$, $SO_2NR^8R^9$ or 1-imidazolyl; $R^8$ and $R^9$ together with the nitrogen atom to which they are attached form a 4-($NR^{11}$)-1-piperazinyl group; and $R^{11}$ is methyl or 2-hydroxyethyl; with the proviso that $R^4$ is not H when $R^1$ is methyl; and $R^5$ is hydrogen.

Especially preferred individual compounds of the invention include:

2-{2-ethoxy-5-[4-(2-hydroxyethyl)-1-piperazinyl-sulphonyl]phenyl}-8-methylquinazolin-4-(3H)-one;

2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)-ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one; and 8-ethylcarbamoyl-2-(2-n-propoxyphenyl)quinazolin-4 (3H)-one.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine. "Lower" refers to 6 or less carbon atoms.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer, and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

EXAMPLE 1

2-[2-Ethoxy-5-(1-piperazinylsulphonyl)phenyl]-8-methoxyquinazolin-4(3H)-one 2-(2-Ethoxyphenyl)-8-methoxyquinazolin-4(3H)-one (Preparation 4; 2.1 g, 0.0071 mol) was added portionwise to stirred chlorosulphonic acid (15 ml) under a nitrogen atmosphere at 0° C. After 18 hours, the mixture was cautiously added dropwise to stirred ice/water (100 g) and the resulting mixture extracted with dichloromethane-methanol (9:1, 10×100 ml). The organic extracts were combined, dried ($MgSO_4$) and evaporated under vacuum. A quantity (1.0 g) of the crude sulphonyl chloride was then added portionwise to a stirred solution of piperazine (2.1 g, 0.0244 mol) in ethanol (30 ml) at room temperature under a nitrogen atmosphere. After 18 hours the mixture was poured into stirred saturated aqueous sodium carbonate solution (100 ml) and the resulting mixture extracted with dichloromethane-methanol (9:1, 10×100 ml). The organic extracts were combined, dried ($MgSO_4$) and evaporated under vacuum to give the title compound, which crystallized from ethanol as a colorless solid (0.8 g, 71%), m.p. 163–165° C.

EXAMPLE 2

2-{2-Ethoxy-5-[4-(2-hydroxyethyl)-1-piperazinylsulphonyl]phenyl}-8-methoxyquinazolin-4(3H)-one The title compound was prepared from 2-(2-ethoxyphenyl)-8-methoxyquinazolin-4(3H)-one (Preparation 4)

and N-(2-hydroxyethyl)piperazine following the procedure of Example 1 and was obtained as a white solid (50%), m.p. 217–218.5° C.

EXAMPLE 3

2-[2-Ethoxy-5-(1-piperazinylsulphonyl)phenyl]-5-methylquinazolin-4(3H)-one

The title compound was prepared from 2-(2-ethoxyphenyl)-5-methylquinazolin-4(3H)-one (Preparation 6) and piperazine following the procedure of Example 1 and was obtained as a white solid (42%), m.p. 234–235° C.

EXAMPLE 4

2-{2-Ethoxy-5-[4-(2-hydroxyethyl)-1-piperazinylsulphonyl]phenyl}-5-methylquinazolin-4(3H)-one The title compound was prepared from 2-(2-ethoxyphenyl)-5-methylquinazolin-4(3H)-one (Preparation 6) and N-(2-hydroxyethyl)piperazine following the procedure of Example 1 and was obtained as a white solid (54%), m.p. 209–211° C.

EXAMPLE 5

2-{2-Ethoxy-5-[4-(2-hydroxyethyl)-1-piperazinylsulphonyl]phenyl}-8-methylquinazolin-4(3H)-one The title compound was prepared from 2-(2-ethoxyphenyl)-8-methylquinazolin-4(3H)-one (Preparation 8) and N-(2-hydroxyethyl)piperazine following the procedure of Example 1 and was obtained as colorless needles (85%), m.p. 247–248° C.

EXAMPLE 6

2-{5-[4-(2-Hydroxyethyl)-1-piperazinylsulphonyl]-2-n-propoxyphenyl}-8-methylquinazolin-4(3H)-one The title compound was prepared from 8-methyl-2(2-n-propoxyphenyl)quinazolin-4(3H)-one (Preparation 10) and N-(2-hydroxyethyl)piperazine following the procedure of Example 1 and was obtained as colorless needles (84%), m.p. 197–201° C.

EXAMPLE 7

8-Methyl-2-[5-(3-piperidinopropylsulphamoyl)-2-n-propoxyphenyl]quinazolin-4(3H)-one The title compound was prepared from 8-methyl-2-(2-n-propoxyphenyl)quinazolin-4(3H)-one (Preparation 10) and 3-piperidinopropylamine following the procedure of Example 1 and was obtained as a colorless solid (73%), m.p. 154–155° C.

EXAMPLE 8

2-(5-Imidazolyl-2-n-propoxyphenyl)-8-methylquinazolin-4(3H)-one

A stirred mixture of 2-(5-bromo-2-n-propoxy-phenyl)-8-methylquinazolin-4(3H)-one (Preparation 11; 0.6 g, 0.0016 mol), anhydrous potassium carbonate (0.22 g, 0.0016 mol), copper bronze (0.1 g, 0.0016 mol), iodine (0.051 g 0.004 mol), imidazole (0.55 g, 0.008 mol) and 1-methyl-2-pyrrolidinone (20 ml) was heated at 180° C. under a nitrogen atmosphere for 6 hours. The mixture was cooled and poured into water (150 ml), then the resulting mixture extracted with a dichloromethane-methanol mixture (9:1, 4×40 ml). The organic extracts were combined, dried ($Na_2SO_4$) and evaporated under vacuum. The semi-solid residue was chromatographed on silica gel (10 g) using a methanol in dichloromethane elution gradient (0–4%). Evaporation of the appropriate fractions gave the title compound which crystallized from ethyl acetate as colorless needles (0.016 g, 3%); Rf 0.5 (silica; dichloromethane-methanol 95:5).

EXAMPLE 9

8-Methyl-2-{5-[2-(4-methyl-1-piperazinylcarbonyl)-ethenyl]-2-n-propoxyphenyl}quinazolin-4(3H)-one A stirred mixture of 2-(5-bromo-2-n-propoxy-phenyl)-8-methylquinazolin-4(3H)-one (Preparation 11; 0.5 g, 0.0013 mol), 1-methyl-4-propenoylpiperazine (Makromol. Chem., 1984, 185, 1525; 0.24 g, 0.0015 mol), palladium diacetate (0.175 g, 0.00077 mol), tri-o-tolylphosphine (0.30 g, 0.001 mol), triethylamine (1 ml) and acetonitrile (25 ml) was heated under reflux under a nitrogen atmosphere for 4 days. The cool mixture was filtered and the filtrate evaporated to dryness under vacuum. The residue was suspended in saturated aqueous sodium carbonate solution (25 ml), the resulting solution extracted with dichloromethane (50 ml) and the organic extract washed with brine (2×30 ml) dried ($Na_2SO_4$) and evaporated under vacuum. Chromatography of the residue on silica gel (10 g), using a methanol in dichloromethane elution gradient (0–4%), gave the title compound which crystallized from hexane-ethyl acetate as a pale pink solid (0.072 g, 12%), m.p. 184–185° C.

EXAMPLE 10 t-Butyl 3-(8-Methylquinazolin-4(3H)-on-2-yl)-4-n-propoxycinnamate

The title compound was prepared from 2-(5-bromo-2-n-propoxyphenyl)-8-methylquinazolin-4(3H)-one (Preparation 11) and t-butyl acrylate following the procedure of Example 9 and was obtained as colorless crystals (18%), m.p. 196–197° C.

EXAMPLE 11

3-(8-Methylquinazolin-4(3H)-on-2-yl)-4-n-propoxycinnamic Acid

2N Aqueous sodium hydroxide solution (2.8 ml) was added to a stirred solution of t-butyl 3-(8-methyl-quinazolin-4(3H)-on-2-yl)-4-n-propoxycinnamate (Example 10; 0.79 g, 0.0018 mol) in methanol (2.8 ml) and the resulting solution heated under reflux for 4 hours. The solvent was removed by evaporation under vacuum, the residue dissolved in water (25 ml) and this solution washed with ethyl acetate (4×30 ml). The aqueous solution was acidified with 2N hydrochloric acid and then extracted with ethyl acetate (3×30 ml). The organic extracts were combined, dried ($Na_2SO_4$) and evaporated under vacuum to give the title compound, which crystallized from ethyl acetate to give a white solid (0.41 g, 60%), m.p. 256–257° C.

EXAMPLE 12

3-[3-(8-Methylquinazolin-4(3H)-on-2-yl)-4-n-propoxy-phenyl]propanoic Acid

A solution of 3-(8-methylquinazolin-4(3H)-on-2-yl)-4-n-propoxycinnaniic acid (Example 11; 0.33 g, 0.00091 mol) in a mixture of ethyl acetate (100 ml), methanol (28.5 ml) and water (1.5 ml), was stirred with 5% palladium on charcoal catalyst under a hydrogen atmosphere at 50 p.s.i. (3.45 bar) for 4 hours. The mixture was then filtered, the filtrate evaporated under vacuum and the residue crystallized from ethyl acetate to give the title compound as an off-white solid (0.224 g, 68%), m.p. 215–216° C.

EXAMPLE 13

2-{2-Ethoxy-5-[4-(2-hydroxyethyl)-1-piperazinyl-sulphonyl]phenyl}quinazolin-4(3H)-one The title compound was prepared from 2-(2-ethoxyphenyl)quinazolin-4(3H)-one (Japanese Patent Application No. 52 51378) and N-(2-hydroxyethyl)-piperazine following the procedure of Example 1 and was obtained as a white solid (78%), m.p. 230–232° C.

EXAMPLE 14

2-[2-Ethoxy-5-(4-methyl-1-piperazinylsulphonyl) phenyl]-quinazolin-4(3H)-one

The title compound was prepared from 2-(2-ethoxyphenyl)quinazolin-4(3H)-one (Japanese Patent Application No. 52 51378) and N-methylpiperazine following the procedure of Example 1 and was obtained as a white solid (79%), m.p. 229–231° C.

EXAMPLE 15

2-[2-Ethoxy-5-(4-carbamoylpiperidinosulphonyl) phenyl]-quinazolin-4(3H)-one

The title compound was prepared from 2-(2-ethoxyphenyl)quinazolin-4(3H)-one (Japanese Patent Application No. 52 51378) and 4-carbamoylpiperidine following the procedure of Example 1 and was obtained as a white solid (68%), m.p. 274–280° C.

EXAMPLE 16

2-(2-Ethoxy-5-morpholinoacetylphenyl)-8-methylquinazolin-4(3H)-one

A solution of 1,4-dioxane dibromide (0.5 g, 0.002 mol) in 1,4-dioxane (10 ml) was added dropwise to a stirred solution of 2-(5-acetyl-2-ethoxyphenyl)-8-methylquinazolin-4(3H)-one (Preparation 15; 0.64 g, 0.002 mol) in 1,4-dioxane (40 ml) and the resulting mixture heated under reflux for 2 hours. The precipitate which formed in the cool reaction mixture was collected by filtration, washed with 1,4-dioxane followed by diethyl ether, and air-dried to give 2-(5-bromoacetyl-2-ethoxyphenyl)-8-methylquinazolin-4(3H)-one, which was used without further purification. The crude bromoacetyl intermediate was suspended in stirred acetonitrile (40 ml) and morpholine (0.174 g, 0.002 mol) added; after 1.5 hours at room temperature, the solvent was evaporated under vacuum. The residue was suspended in water (20 ml) and the suspension extracted with dichloromethane (3×20 ml), then the extracts were combined, dried ($Na_2SO_4$) and evaporated under vacuum. The residue was chromatographed on silica gel using a methanol in dichloromethane elution gradient (0–1%) and then the product crystallized from ethyl acetate-hexane to give the title compound as a white powder (0.29 g, 36%), m.p. 172–173° C.

EXAMPLE 17

2-[2-Ethoxy-5-(1-hydroxy-2-morpholinoethyl) phenyl]-8-methylquinazolin-4(3H)-one 2-(2-Ethoxy-5-morpholinoacetylphenyl)-8-methylquinazolin-4(3H)-one (Example 16; 0.2 g, 0.00049 mol) was suspended in stirred ethanol (30 ml) and the mixture treated with sodium borohydride (0.0018 g, 0.00049 mol). After 18 hours at room temperature, the solvent was evaporated under vacuum. The residue was suspended in saturated aqueous sodium carbonate solution (30 ml) and the suspension extracted with ethyl acetate (3×20 ml). The extracts were combined, dried ($Na_2SO_4$) and evaporated under vacuum, then the residue crystallized from ethyl acetate-hexane to give the title compound as colorless plates (0.14 g, 70%), m.p. 145–147° C.

EXAMPLE 18

8-Carbamoyl-2-(2-ethoxyphenyl)quinazolin-4(3H)-one

A stirred mixture of 3-carbamoyl-2-(2-ethoxybenzamido) benzamide (Preparation 18; 1 g, 0.003 mol) sodium hydroxide (0.61 g, 0.015 mol), water (30 ml) and ethanol (7 ml) was heated under reflux for 1 hour. The cool solution was washed with dichloromethane (3×30 ml), acidified to pH 1 with 2N hydrochloric acid and the resulting precipitate collected by filtration. The solid was suspended in saturated aqueous sodium carbonate solution (60 ml) and this suspension extracted with dichloromethane-methanol (98:2, 3×100 ml). The extracts were combined, dried ($Na_2SO_4$) and evaporated under vacuum, then the residue triturated with diethyl ether (50 ml) to give the title compound as a white solid (0.72 g, 78%), m.p. 252–254° C.

EXAMPLE 19

8-Carbamoyl-2-{2-ethoxy-5-[4-(2-hydroxyethyl)-1-piperazinylsulphonyl]phenyl}quinazolin-4 3H)-one The title compound was prepared from 8-carbamoyl-2-(2-ethoxyphenyl)quinazolin-4(3H)-one (Example 18) and N-(2-hydroxyethyl)piperazine following the procedure of Example 1 and was obtained as a white hemi-hydrate (120), m.p. 268–269° C.

EXAMPLE 20

8-Carbamoyl-2-(2-n-propoxyphenyl)quinazolin-4 (3H)-one 2-n-Propoxybenzoyl chloride (7.27 g, 0.366 mol) was added dropwise to a stirred suspension of 2-amino-3-carbamoylbenzamide (Preparation 17; 2.63 g, 0.0147 mol) in pyridine (50 ml) at 0° C. The mixture was stirred at room temperature for 3 days, then the solvent evaporated under vacuum. The residue was treated with water (100 ml) and, on chilling the solution, colorless crystals formed. The product was collected by filtration and then suspended in a stirred mixture of sodium hydroxide (1.73 g, 0.043 mol), water (90 ml) and ethanol (20 ml). The mixture was heated under reflux for 3 hours, allowed to cool and filtered. The filtrate was acidified to pH 2 with concentrated hydrochloric acid and extracted with a methanol-dichloromethane mixture (2:98, 3×100 ml). The organic extracts were combined, washed sequentially with saturated aqueous sodium carbonate solution (3×100 ml) and brine (3×50 ml), dried ($Na_2SO_4$) and evaporated under vacuum. Crystallization of the residue from ethyl acetate-methanol gave the title compound as a white solid (1 g, 40%), m.p. 226–227° C.

On standing, the aqueous sodium carbonate washings deposited a precipitate which was collected by filtration. This solid was dissolved in 1N hydrochloric acid (100 ml) and the solution extracted with dichloromethane (3×20 ml).

The organic extracts were combined, dried (Na$_2$SO$_4$) and evaporated under vacuum, then the residue crystallized from ethyl acetate to give 8-carboxy-2-(2-n-propoxyphenyl) quinazolin-4(3H)-one (0.3 g, 11%) as colorless needles, m.p. 195–197° C.

EXAMPLE 21

8-Ethylcarbamoyl-2-(2-n-propoxyphenyl)quinazolin-4(3H)-one

A solution of oxalyl chloride (0.94 g, 0.0074 mol) in dichloromethane (10 ml) was added dropwise to a stirred solution of 8-carboxy-2-(2-n-propoxyphenyl)quinazolin-4 (3H)-one (see Example 20; 1.2 g, 0.0037 mol) in dichloromethane (40 ml) and the resulting mixture stirred for a further 18 hours. The solvent was evaporated under vacuum and the residue triturated with hexane to give the acyl chloride as a yellow solid. This solid was dissolved in dichloromethane (20 ml) and the solution added dropwise to a stirred solution of ethylamine (2.1 g, 0.047 mol) in dichloromethane (40 ml) at 0° C. After 18 hours, the reaction mixture was filtered and evaporated under vacuum. The residue was dissolved in dichloromethane (20 ml) and the solution washed sequentially with 2N hydrochloric acid (3×20 ml), saturated aqueous sodium carbonate solution (3×20 ml) and brine (2×20 ml), then dried (Na$_2$SO$_4$). Evaporation under vacuum, chromatography of the residue on silica gel (12 g) using a methanol in dichloromethane elution gradient (0–3%), and crystallization of the product from ethyl acetate-hexane gave the title compound as colorless crystals (0.016 g, 1%), m.p. 161–162° C.

EXAMPLE 22

2-(5-Acetyl-2-n-propoxyphenyl)-8-methylquinazolin-4(3H)-one

The title compound was prepared from 2-(5-acetyl-2-n-propoxybenzamido)-8-methylbenzamide (Preparation 21) following the procedure of Example 18 and was obtained as white needles (4%), m.p. 183–184° C.

EXAMPLE 23

2-(2-Propoxyphenyl)quinazolin-4(3H)-one a) A mixture of 2-propoxybenzoic acid (5 g) in thionyl chloride (20 ml) was heated under reflux for three hours. Thionyl chloride was removed under reduced pressure and the residue was azeotroped with toluene to yield the acid chloride as a yellow oil (5.5 g). A solution of anthranilamide (3.77 g) in a mixture of saturated aqueous sodium acetate (20 ml) and acetic acid (20 ml) was added to the yellow oil in acetone (4 ml). The resulting solution was stirred at ambient temperature for one hour to yield as a light brown precipitate 2-(2-propoxybenzamido)benzamide, 3.78 g. A sample recrystallized from ether had m.p. 149–150° C.

b) 2-(2-Propoxybenzamido)benzamide (2.73 g) was added to a refluxing mixture of 2 Normal aqueous sodium hydroxide (55 ml) and pyridine (2 ml). The resulting solution was stirred under reflux for 15 minutes and was then poured onto ice (150 ml) and acidified with concentrated hydrochloric acid to yield a sample of the title compound, 2.28 g, m.p. 88–89° C. This together with another sample (0.77 g) similarly prepared was recrystallized from ethanol/water to yield the pure title compound as a white solid, 2.57 g, m.p. 89–90° C.

EXAMPLE 24

7-Methylthio-2-(2-propoxyphenyl)quinazoline-4(3H)-one a) Methyl mercaptan was bubbled through a solution of copper sulphate pentahydrate (50 g) in water (200 ml) for 30 minutes to form cuprous thiomethoxide (11.70 g) as a precipitate, which was collected and washed successively with water, methanol and ether.

A solution of sodium nitrate (3.70 g) in water (15 ml) was added with cooling (30–40 C.) to a stirred suspension of 4-amino-2-nitrobenzoic acid (9.11 g) in water (50 ml) and concentrated sulphuric acid (10 ml) in order to prepare the diazonium salt. The resultant solution was added dropwise during 30 minutes to a cooled (4° C.) slurry of cuprous thiomethoxide (11.7 g) in water (20 ml) and the reaction mixture was stirred for 1.5 hours at ambient temperature.

The reaction mixture was extracted well with chloroform (a total of 650 ml) and the chloroform extracts were washed with 2 Normal hydrochloric acid (2×25 ml), dried (magnesium sulphate) and evaporated under reduced pressure to a residue. The residue was dissolved in dilute aqueous sodium hydroxide and 2 Normal hydrochloric acid was added to precipitate 4-methylthio-2-nitrobenzoic acid (3.71 g) m.p. 172.5° C.

b) A stirred solution of 4-methylthio-2-nitrobenzoic acid (4.56 g) and thionyl chloride (2.77 g) in benzene (65 ml) was heated under reflux for 1.5 hours. Aqueous ammonia (10 ml) was added dropwise to the stirred cooled (5° C.) reaction mixture, which was then stirred with cooling for 45 minutes. Benzene was removed under reduced pressure and the residual solid was washed with water and recrystallized to yield 4-methylthio-2-nitrobenzamide, (2.35 g), m.p. 176°–8° C.

c) A stirred mixture of 4-methylthio-2-nitrobenzamide (2.47 g), stannous chloride dihydrate (13.13 g) and ethanol (90 ml) was heated under reflux under nitrogen for one hour. The reaction mixture was added to ice and neutralized to pH 7 with 5% aqueous sodium bicarbonate solution and the resultant mixture was extracted with ethyl acetate:methanol (9:1, 6×199 ml). The combined extracts were washed with brine, dried (magnesium sulphate) and evaporated under reduced pressure to yield 2-amino-4-methylthiobenzamide (1.84 g), m.p. 172.5°–173.5° C.

d) A solution of 2-propoxybenzoyl chloride (0.76 g) in acetonitrile (6 ml) was added dropwise to an ice-cold stirred mixture of 2-amino-4-methylthiobenzamide (0.70 g) and triethylamine (0.39 g) in acetonitrile (6 ml). The reaction mixture was stirred at ambient temperature for 17 hours. Acetonitrile was removed under reduced pressure and the residual solid was washed with water and recrystallized from ethanol to yield 4-methylthio-2-(2-propoxybenzamido)benzamide (0.49 g), m.p. 178.5°–181° C. A further sample (0.40 m.p. 182°–4° C.) was prepared by evaporating the ethanolic mother liquor and recrystallizing the residue from ethanol.

e) A stirred solution of 4-methylthio-2-(2-propoxybenzamido)benzamide (0.85 g) and pyridine (1 ml) in 2 Normal aqueous sodium hydroxide was heated under reflux for 2 hours. The cooled reaction mixture was acidified with concentrated hydrochloric acid and the resultant mixture was extracted with chloroform (3×25 ml). The combined extracts were washed with water and then brine, dried (magnesium sulphate) and evaporated under reduced pressure to yield a solid which was recrystallized from ethanol to yield the title compound, 0.61 g, m.p. 156.5°–158.5° C.

EXAMPLE 25

7-Nitro-2-(2-Propoxyphenyl)-4(3H)-quinazolinone

Methyl 4-nitroanthranilate (2.0 g, prepared from 4-nitroanthranalic acid by treatment with dry HCl in refluxing methanol) was added to a solution of 2-propoxybenzoyl chloride (2.0 g) and triethylamine (1.0 g) in dry tetrahydrofuran (5 ml) at 0° C. After stirring at room temperature for 60 minutes, water was added and the mixture partitioned between water and dichloromethane. The organic layer was separated, dried (magnesium sulphate) and evaporated to give a solid (3.6 g). This material (1.0 g) was dissolved in 50 ml of saturated methanolic ammonia and the solution heated in a pressure vessel at 100° C. for 18 hours. Evaporation of the solvents and recrystallization of the residue from dichloromethane-petroleum ether gave 7-nitro-(2-propoxyphenyl)-4(3H)-quinazolinone, 0.9 g, m.p. 138° C.

EXAMPLE 26

7-Amino-2-(2-Propoxyphenyl)-4(3H)-quinazolinone

A stirred solution of 7-nitro-2-(2-propoxyphenyl)-4(3H)-quinazolinone (3.0 g) in dry methanol (450 ml) was treated sequentially under a carbon dioxide atmosphere with 5% Pd/C(1.5 g) and anhydrous ammonium formate (2.8 g). After 60 minutes solids were removed by filtration and the filtrate evaporated to dryness. The residue was partitioned between water and dichloromethane, the organic layer separated, dried (magnesium sulphate) and evaporated. The residue was recrystallized from diethyl ether-petroleum ether to give 7-amino-2-(2-propoxyphenyl)-4(3H)-quinazolinone, 2.7 g, m.p. 185° C.

EXAMPLE 27

7-Methylamino-2-(2-Propoxyphenyl)-4(3H)-quinazolinone 7-amino-2-(2-propoxyphenyl)-4(3H)-quinazolinone (0.5 g) was heated under reflux in trimethylortho-formate (5 ml) for 22 hours. The reaction mixture was evaporated to dryness, the residue dissolved in dry tetrahydrofuran and treated with sodium borohydride (0.3 g) and 4A molecular sieves for 24 hours. The reaction mixture was partitioned between water and dichloromethane, the organic layer separated, dried (magnesium sulphate) and evaporated. The residue was recrystallized from dichloromethane-diethyl ether to give 7-methylamino-2-(2-propoxyphenyl)-4(3H)-quinazolinone 0.17 g, m.p. 204°–205° C.

EXAMPLE 28

Pharmaceutical compositions for oral administration are prepared by combining the following:

|  | % w/w | | |
| --- | --- | --- | --- |
| 2-(2-Propoxyphenyl)quinazolin-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 29

A pharmaceutical composition for parenteral administration is prepared by dissolving the title compound of Example 4 (0.02 g) in polyethylene glycol 300 (25 ml) with heating. This solution is then diluted with water for injections Ph. Eur. (to 100 ml). The solution is then sterilized by filtration through a 0.22 micron membrane filter and sealed in sterile containers.

Preparation 1

3-Methoxy-2-nitrobenzamide

3-Methoxy-2-nitrobenzoic acid (10.0 g, 0.051 mol) was added portionwise to stirred thionyl chloride (40 ml) and the resulting mixture heated under reflux for 2 hours. The solution obtained was allowed to cool and the solvent evaporated under vacuum. The resulting yellow solid was azeotroped with toluene (2×100 ml) before being dissolved in tetrahydrofuran (100 ml); this solution was added dropwise over 0.5 hour to stirred saturated aqueous ammonia solution (100 ml) at 0° C. After a further 0.25 hour, the mixture was evaporated to dryness under vacuum to give the title compound as a pink solid (9.48 g, 95%), m.p. 212–214° C.

Preparation 2

2-Amino-3-methoxybenzamide

3-Methoxy-2-nitrobenzamide (7.0 g, 0.038 mol) was dissolved in ethanol (150 ml) and the solution stirred with Raney nickel catalyst (0.5 g) under a hydrogen atmosphere at 50 p.s.i. (3.45 bar) for 4 hours. The catalyst was removed by filtration and the solvent removed by evaporation under vacuum to give the title compound, after crystallization from ethyl acetate-hexane, as a colourless solid (6.3 g, 83%), m.p. 140–141° C.

Preparation 3

2-(Ethoxybenzamido)-3-methoxybenzamide

2-Ethoxybenzoyl chloride (8.9 g, 0.048 mol) was added dropwise to a stirred solution of 2-amino-3-methoxybenzamide (4.0 g, 0.024 mol) in pyridine (35 ml) under a nitrogen atmosphere at 0° C. After 20 hours at room temperature, the solvent was removed by evaporation under vacuum, the residue dissolved in dichloromethane (100 ml) and the solution washed successively with 2N hydrochloric acid (2×100 ml) and saturated aqueous sodium hydrogen carbonate solution (2×100 ml). The organic phase was dried ($MgSO_4$) and evaporated under vacuum, then the resulting oil chromatographed on silica gel (40 g), eluting with a mixture of methanol in-dichloromethane (2%), to give the title compound as a colourless solid (4.1 g, 54%), m.p. 177–179° C.

Preparation 4

2-(2-Ethoxyphenyl)-8-methoxyquinazolin-4(3H)-one

A stirred mixture of 2-(2-ethoxybenzamido)-3-methoxybenzamide (2.6 g, 0.0083 mol), anhydrous potassium carbonate (2.33 g, 0.017 mol), hydrogen peroxide (30%, 4 ml), ethanol (40 ml) and water (80 ml) was heated under reflux for 1 hour. The mixture was allowed to cool and poured into a mixture of water (200 ml) and dichloromethane (100 ml), then the aqueous phase separated, acidified to pH 4 by the addition of 2N hydrochloric acid and extracted with dichloromethane (2×100 ml). The organic solutions were combined, dried ($MgSO_4$) and evaporated under vacuum to give the title compound, which crystallized from ethyl acetate as a colourless solid (2.8 g, 83%), m.p. 198–199° C.

Preparation 5

2-(2-Ethoxybenzamido)-6-methylbenzamide

A mixture of 2-amino-6-methylbenzamide (UK Patent Application No 1,276,359; 5.49 g, 0.0365 mol), 2-ethoxybenzoyl chloride (7.67 g, 0.0415 mol) and pyridine (100 ml) was stirred at room temperature for 20 hours. The solvent was then removed by evaporation under vacuum and the residue dissolved in dichloromethane (200 ml). The solution was washed with saturated aqueous sodium carbonate solution (200 ml) and the aqueous phase back-extracted with further dichloromethane (2×100 ml). The organic solutions were combined, washed successively with 2N hydrochloric acid (3×100 ml) and brine (100 ml), then dried ($Na_2SO_4$) and evaporated under vacuum to give the title compound, which recrystallized from ethyl acetate as a colourless solid (6.86g, 63%), m.p. 166–168° C.

Preparation 6
2-(2-Ethoxyphenyl)-5-methylquinazolin-4(3H)-one
The title compound was prepared from 2-(2-ethoxybenzamido)-6-methylbenzamide following the procedure of Preparation 4 and was obtained as a colourless solid (30%), m.p. 148–150° C.

Preparation 7
2-(2-Ethoxybenzamido)-3-methylbenzamide
The title compound was prepared from 2-amino-3-methylbenzamide (Chem. Pharm. Bull., 1988, 36, 2955) and 2-ethoxybenzoyl chloride following the procedure of Preparation 5 and was obtained as colourless crystals (71%), m.p. 197–200° C.

Preparation 8
2-(2-Ethoxyphenyl)-8-methylquinazolin-4(3H)-one
A mixture of 2-(2-ethoxybenzamido)-3-methylbenzamide (1.6 g, 0.0053 mol) and anhydrous zinc chloride (2.29 g, 0.016 mol) was heated at 210° C. for 5 minutes, then allowed to cool. The residue was dissolved in dichloromethane-methanol (90:10, 200 ml) and this solution washed with an aqueous solution of ethylenediamine tetraacetic acid disodium salt (12 g in 400 ml of water). The aqueous phase was then extracted with a mixture of dichloromethane-methanol (90:10, 2×50 ml) and the organic solutions combined, dried ($Na_2SO_4$) and evaporated under vacuum. The residue crystallized from ethanol to give the title compound as colourless needles (0.6 g, 40%), m.p. 177–180° C.

Preparation 9
3-Methyl-2-(2-n-propoxybenzamido)benzamide
The title compound was prepared from 2-amino-3-methylbenzamide and 2-n-propoxybenzoyl chloride following the procedure of Preparation 5 and was obtained as a colourless solid (71%), m.p. 140–142° C.

Preparation 10
8-Methyl-2-(2-n-propoxyphenyl)quinazolin-4(3H)-one
The title compound was prepared from 3-methyl-2-(2-n-propoxybenzamido)benzamide following the procedure of Preparation 4 and was obtained as a colourless solid (77%), m.p. 129–132° C.

Preparation 11
2-(5-Bromo-2-n-propoxyphenyl)-8-methylquinazolin-4(3H)-one
Bromine (3.2 g, 0.020 mol) was added dropwise to a stirred solution of 8-methyl-2-(2-n-propoxyphenyl)-quinazolin-4(3H)-one (3 g, 0.010 mol) in glacial acetic acid (45 ml) at 95° C. The resulting suspension was heated at 105° C. for 18 hours and then evaporated under vacuum. The resulting solid was dissolved in dimethylformamide (25 ml) and the stirred solution treated dropwise with a solution of N-bromosuccinimide (0.89 g, 0.0051 mol) in dimethylformamide (25 ml). After 1 hour at ambient temperature, the solvent was evaporated under vacuum and the residue dissolved in ethyl acetate (50 ml). This solution was washed with saturated aqueous sodium carbonate solution (50 ml), dried ($Na_2SO_4$) and evaporated under vacuum. The residue was chromatographed on silica gel (30 g) using a methanol in dichloromethane elution gradient (0–100%) to give the title compound as a white solid (1.67 g, 45%), m.p. 179–180° C.; Rf 0.7 (silica; dichloromethane-methanol; 99:1). This material was used without any further purification.

Preparation 12
Methyl 5-Acetyl-2-ethoxybenzoate
A stirred mixture of methyl 5-acetyl-2-hydroxy-benzoate (10 g, 0.052 mol), iodoethane (16.4 g, 0.104 mol), anhydrous potassium carbonate (14.4 g, 0.104 mol) and 2-butanone (200 ml) was heated under reflux for 3 days. The solvent was then removed by evaporation under vacuum, the residue dissolved in water (200 ml) and this solution extracted with ethyl acetate (4×200 ml). The organic fractions were combined, washed with brine (2×200 ml), dried ($Na_2SO_4$) and evaporated under vacuum, then the residue chromatographed on silica gel (130 g) using a methanol in dichloromethane elution gradient (0–1%). Crystallization of the product from ethyl acetate-hexane gave the title compound as colourless crystals (10.15 g, 88%), m.p. 50–55° C.

Preparation 13
5-Acetyl-2-ethoxybenzoic Acid
A stirred solution of methyl 5-acetyl-2-ethoxy-benzoate (9.6 g, 0.043 mol) in a mixture of 1,4-dioxane (80 ml) and water (80 ml) was treated with 5N aqueous sodium hydroxide solution (44 ml, 0.217 mol). The mixture was stirred at room temperature for 18 hours then the solvents evaporated under vacuum. The residue was dissolved in water (100 ml), then this solution was acidified to pH 1 with concentrated hydrochloric acid and extracted with ethyl acetate (4×100 ml). The organic extracts were combined, dried ($Na_2SO_4$) and evaporated under vacuum. Crystallization of the residue from ethyl acetate gave the title compound as a colourless solid (5.4 g, 60%), m.p. 122–125° C.

Preparation 14
2-(5-Acetyl-2-ethoxybenzamido)-3-methylbenzamide
Oxalyl chloride (3.66 g, 0.0288 mol) was added dropwise to a stirred solution of 5-acetyl-2-ethoxy-benzoic acid (3 g, 0.00144 mol) and dimethylformamide (0.1 ml) in dichloromethane (15 ml). The mixture was stirred at room temperature for 3 hours, then the solvent evaporated under vacuum and the residue azeotroped with hexane (3×50 ml). The crude acyl chloride was dissolved in dichloromethane (20 ml) and the solution added dropwise to a stirred solution of 2-amino-3-methylbenzamide (2.16 g, 0.0144 mol) in pyridine (40 ml) at 0° C. The mixture was allowed to warm to room temperature and stirred for a further 18 hours. The solvent was removed by evaporation under vacuum, the residue dissolved in dichloromethane (50 ml) and this solution then washed with saturated aqueous sodium carbonate solution (50 ml), 2N hydrochloric acid (50 ml) and brine (50 ml), then dried ($Na_2SO_4$) and evaporated under vacuum. Trituration of the residue with diethyl ether gave the title compound as a white solid (2.14 g, 44%), m.p. 214–216° C.

Preparation 15
2-(5-Acetyl-2-ethoxyphenyl)-8-methylquinazolin-4(3H)-one
The title compound was prepared from 2-(5-acetyl-2-ethoxybenzamido)-3-methylbenzamide following the procedure of Preparation 4 and was obtained as a colourless solid (92%), m.p. 196–197° C.

Preparation 16
3-Carbamoyl-2-nitrobenzamide

Oxalyl chloride (11.9 g, 0.094 mol) was added dropwise to a stirred solution of 2-nitroisophthalic acid (5 g, 0.0245 mol) and dimethylformamide (0.1 ml) in dichloromethane (100 ml). After 6 hours at room temperature, the solvent was removed by evaporation under vacuum. The residue was triturated with hexane (3×20 ml) and dissolved in tetrahydrofuran (30 ml), then this solution was added dropwise to stirred aqueous ammonium hydroxide solution (30 ml) at 0° C. After 18 hours at room temperature, the mixture was evaporated to dryness under vacuum and water (20 ml) added to the residue. Filtration followed by crystallization of the crude product from a mixture of dimethylformamide-methanol-ethyl acetate gave the title compound as colourless crystals (4 g, 80%), m.p. 283–285° C.

Preparation 17
2-Amino-3-carbamoylbenzamide

3-Carbamoyl-2-nitrobenzamide (0.6 g, 0.0029 mol) was dissolved in ethanol (50 ml) and the solution stirred with 5% palladium on charcoal catalyst (0.1 g) under a hydrogen atmosphere at 50 p.s.i. (3.45 bar) and 50° C. for 5 hours. The catalyst was removed by filtration, the solvent evaporated under vacuum and the residue crystallized from water to give the title compound as a grey solid (0.26 g, 50%), m.p. 284–288° C.

Preparation 18
3-Carbamoyl-2-(2-ethoxybenzamido)benzamide

The title compound was prepared from 2-amino-3-carbamoylbenzamide and 2-ethoxybenzoyl chloride following the procedure of Preparation 5 and was obtained as colourless crystals (33%), m.p. 224–225° C.

Preparation 19
Methyl 5-Acetyl-2-n-propoxybenzoate

A stirred mixture of methyl 5-acetyl-2-hydroxy-benzoate (10 g, 0.0515 mol), 1-iodopropane (10.5 g, 0.0618 mol), anhydrous potassium carbonate (14.2 g, 0.103 mol) and 2-butanone (200 ml) was heated under reflux for 18 hours. A further quantity of 1-iodopropane (10.5 g, 0.0618 mol) was then added and heating under reflux continued for a further 24 hours. The solvent was removed by evaporation under vacuum and the residue partitioned between water (200 ml) and ethyl acetate (200 ml). The aqueous phase was extracted with ethyl acetate (2×100 ml), then the organic solutions combined, dried ($Na_2SO_4$) and evaporated under vacuum. The residue was chromatographed on silica gel (120 g) using a methanol in dichloromethane elution gradient (0–1%), then crystallization of the product from ethyl acetate-hexane gave the title compound as white crystals (6.85 g, 56%), m.p. 49° C.

Preparation 20
5-Acetyl-2-n-propoxybenzoic Acid

The title compound was prepared from methyl 5-acetyl-2-n-propoxybenzoate following the procedure of Preparation 13 and was obtained as colourless crystals (66%), m.p. 104° C.

Preparation 21
2-(5-Acetyl-2-n-propoxybenzamido)-8-methylbenzamide

The title compound was prepared from 2-amino-3-methylbenzamide and 5-acetyl-2-n-propoxybenzoyl chloride following the procedure of Preparation 5 and was obtained as white crystals (11%), m.p. 189–190° C.

It will be understood that various changes and modifications can be made in the details of procedure, formulation and use without departing from the spirit of the invention, especially as defined in the following claims.

We claim:

1. A method of treating a patient having precancerous lesions sensitive to a compound of the formula below in need of treatment, comprising administering to the patient a pharmacologically effective amount of a compound of the formula:

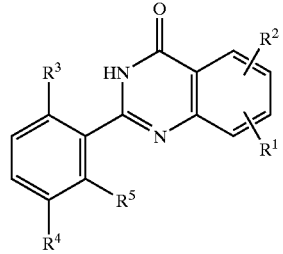

wherein $R^1$ and $R^2$ are independently hydrogen, lower alkyl, lower alkoxy, lower alkyl thio, nitro, —$CONR^6R^7$, or —$NR^6R^7$; and $R^6$ and $R^7$ are independently hydrogen or lower alkyl optionally substituted by hydroxy provided that the carbon atom adjacent to the nitrogen atom is not substituted by hydroxy;

$R^3$ is hydrogen, lower alkyl or lower alkoxy;

$R^4$ is hydrogen, $C_2$–$C_4$ alkanoyl optionally substituted with $NR^8R^9$, (hydroxy) $C_2$–$C_4$ alkyl optionally substituted with $NR^8R^9$, CH=$CHCO_2R^{10}$, CH=$CHCONR^8R^9$, $CH_2CH_2CO_2R^{10}$, $CH_2CH_2CONR^8R^9$, $SO_2NR^8R^9$, $SO_2NH(CH_2)_nNR^8R^9$ or imidazolyl; and $R^8$ and $R^9$ are independently hydrogen or lower alkyl or together with the nitrogen to which they are attached form a pyrrolidino, piperidino, morpholino or 4-($NR^6$)-1-piperazinyl group wherein any of said groups is optionally substituted with $CONR^6R^7$; n is 2, 3 or 4; and $R^5$ is lower alkoxy, lower alkenoxy, cyclo(lower)alkyl (lower)alkoxy, phenyl(lower)alkoxy, or phenyl(lower) alkoxy with the alkoxy substituted by 1 to 6 fluoro groups.

2. A method of inhibiting the growth of neoplastic cells sensitive to a compound of the formula below, comprising exposing said cells to an effective amount of a compound of the formula:

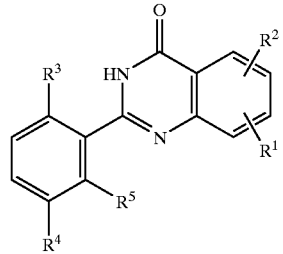

wherein $R^1$ and $R^2$ are independently hydrogen, lower alkyl, lower alkoxy, lower alkyl thio, nitro, —$CONR^6R^7$, or —$R^6R^7$; and $R^6$ and $R^7$ are independently hydrogen or lower alkyl optionally substituted by hydroxy provided that the carbon atom adjacent to the nitrogen atom is not substituted by hydroxy;

$R^3$ is hydrogen, lower alkyl or lower alkoxy;

$R^4$ is hydrogen, $C_2$–$C_4$ alkanoyl optionally substituted with $NR^8R^9$, (hydroxy) $C_2$–$C_4$ alkyl optionally substituted with $NR^8R^9$, CH=$CHCO_2R^{10}$, CH=$CHCONR^8R^9$, $CH_2CH_2CO_2R^{10}$, $CH_2CH_2CONR^8R^9$, $SO_2NR^8R^9$, $SO_2NH(CH_2)_nNR^8R^9$ or imidazolyl; and $R^8$ and $R^9$ are independently hydrogen or lower alkyl or together with the nitrogen to which they are attached form a pyrrolidino, piperidino, morpholino or 4-(NR$^6$)-1-piperazinyl group wherein any of said groups is optionally substituted with CONR$^6$R$^7$; n is 2, 3 or 4; and R$^5$ is lower alkoxy, lower alkenoxy, cyclo(lower)alkyl (lower)alkoxy, phenyl(lower)alkoxy, or phenyl(lower) alkoxy with the alkoxy substituted by 1 to 6 fluoro groups.

3. A method for regulating apoptosis in human cells, comprising exposing said cells to an effective amount of the formula:

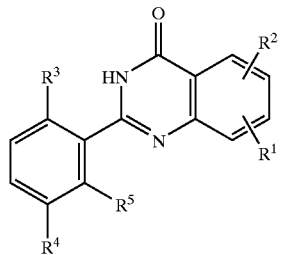

wherein R$^1$ and R$^2$ are independently hydrogen, lower alkyl, lower alkoxy, lower alkyl thio, nitro, —CONR$^6$R$^7$, or —NR$^6$R$^7$; and R$^6$ and R$^7$ are independently hydrogen or lower alkyl optionally substituted by hydroxy provided that the carbon atom adjacent to the nitrogen atom is not substituted by hydroxy;

R$^3$ is hydrogen, lower alkyl or lower alkoxy;

R$^4$ is hydrogen, C$_2$–C$_4$ alkanoyl optionally substituted with NR$^8$R$^9$, (hydroxy)C$_2$–C$_4$ alkyl optionally substituted with NR$^8$R$^9$, CH=CHCO$_2$R$^{10}$, CH=CHCONR$^8$R$^9$, CH$_2$CH$_2$CO$_2$R$^{10}$, CH$_2$CH$_2$CONR$_8$R$_9$, SO$_2$NR$^8$R$^9$, SO$_2$NH(CH$_2$)$_2$NR$^8$R$^9$ or imidazolyl; and R$^8$ and R$^9$ are independently hydrogen or lower alkyl or together with the nitrogen to which they are attached form a pyrrolidino, piperidino, morpholino or 4-(NR$^6$)-1-piperazinyl group wherein any of said groups is optionally substituted with CONR$^6$R$^7$; n is 2, 3 or 4; and R$^5$ is lower alkoxy, lower alkenoxy, cyclo(lower)alkyl (lower)alkoxy, phenyl(lower)alkoxy, or phenyl(lower) alkoxy with the alkoxy substituted by 1 to 6 fluoro groups.

* * * * *